United States Patent [19]

Grotenhuis

[11] Patent Number: 4,668,223
[45] Date of Patent: May 26, 1987

[54] SYRINGE

[75] Inventor: Gerrit Grotenhuis, Olst, Netherlands

[73] Assignee: Duphar International Research B.V., Weesp, Netherlands

[21] Appl. No.: 825,935

[22] Filed: Feb. 4, 1986

[30] Foreign Application Priority Data

Feb. 7, 1985 [NL] Netherlands .................. 8500341

[51] Int. Cl.$^4$ .............................................. A61M 5/00
[52] U.S. Cl. .................................... 604/191; 604/218
[58] Field of Search ............... 604/191, 192, 218, 89, 604/90, 91, 187

[56] References Cited

U.S. PATENT DOCUMENTS

| | | | |
|---|---|---|---|
| 4,439,184 | 3/1984 | Wheeler | 604/90 |
| 4,496,344 | 1/1985 | Kamstra | 604/191 X |
| 4,529,403 | 7/1985 | Kamstra | 604/191 X |
| 4,573,971 | 3/1986 | Kamstra | 604/191 |

Primary Examiner—John D. Yasko
Attorney, Agent, or Firm—Stevens, Davis, Miller & Mosher

[57] ABSTRACT

The invention relates to an injection syringe having an ampoule in which a plunger and a sealing stopper are provided, and a needle holder comprising a collar to be provided on the ampoule in a sealing manner and a sleeve closed at its front end by means of a wall. The end wall has on its outside a neck for connecting an injection needle, an aperture being recessed in the front end of the sleeve. The side wall of the sleeve has at least one longitudinal duct which, over a small part of its length, is in open communication with the room bounded by the inner walls of the sleeve.

11 Claims, 9 Drawing Figures

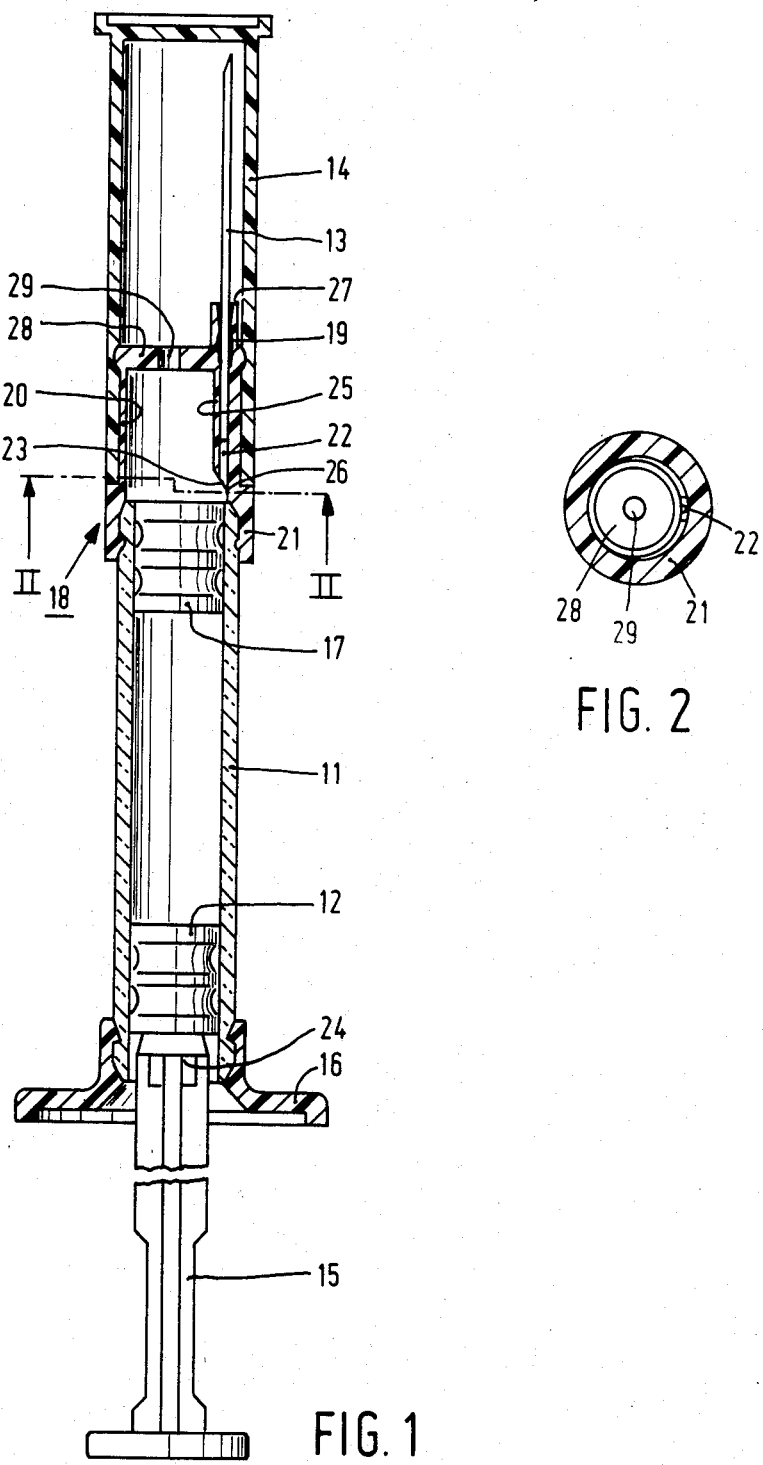

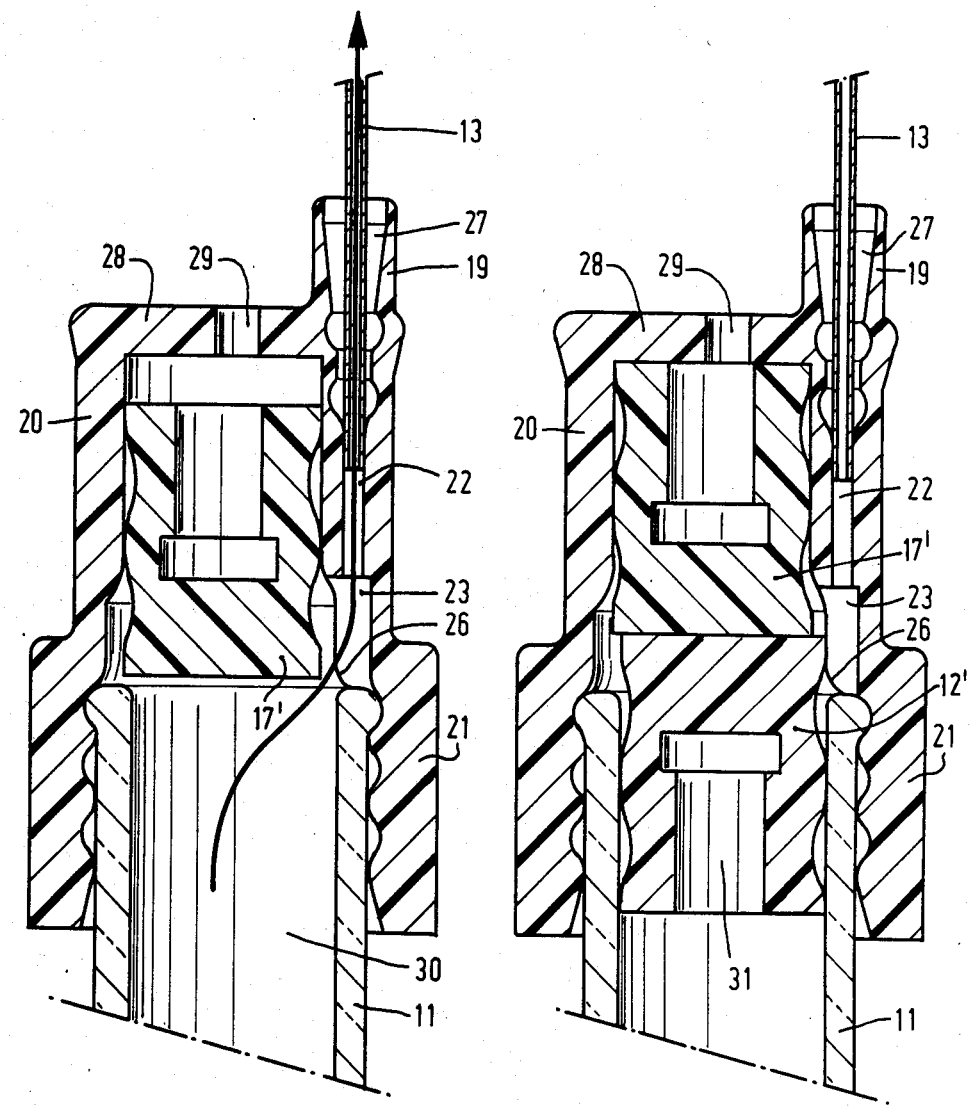

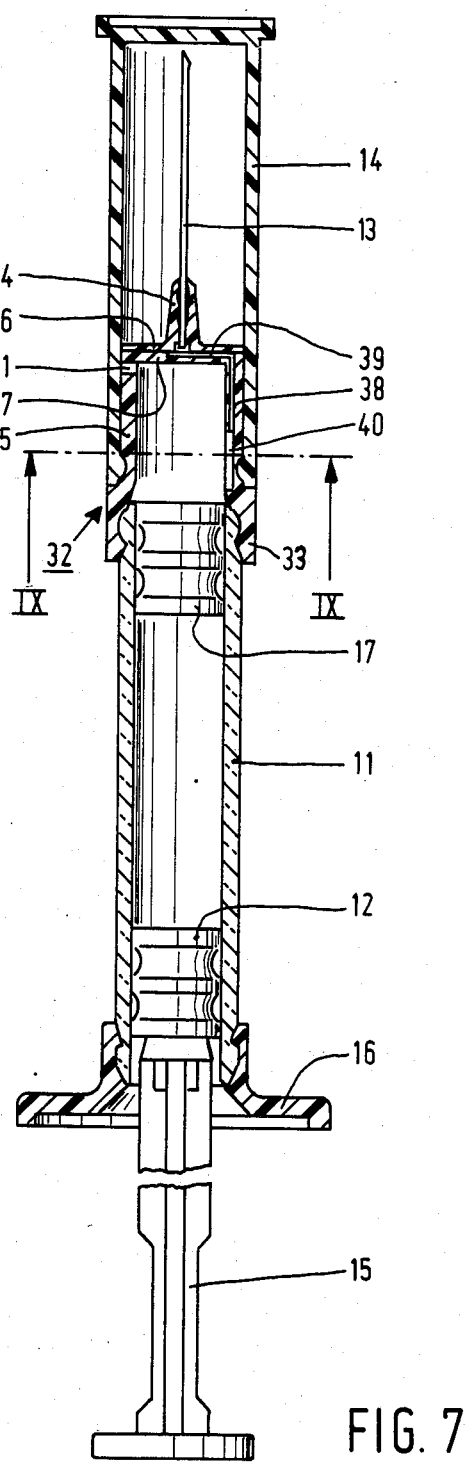
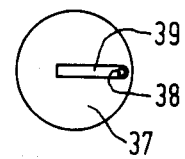
FIG. 8
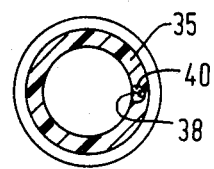
FIG. 9
FIG. 7

SYRINGE

The invention relates to an injection syringe comprising a hollow cylindrical ampoule which is open at both ends, a plunger which is movable in the ampoule and seals the same, a sealing stopper the dimensions of which are such that it can be provided in a sealing manner in the front end of the ampoule, optionally a separating stopper to be provided in the ampoule so as to be movable and in a sealing manner in order to be able to keep two different injection liquids, if present in the ampoule, separated from each other prior to use of the syringe, and a needle holder comprising a collar connected to the front end of the ampoule in a sealing manner, and an inwardly substantially cylindrical sleeve closed at its front end by means of a wall. The end wall comprises on the outside a neck in the aperture of which or to which an injection needle is or can be connected in a sealing manner. The side wall of the sleeve comprises over approximately the full length a longitudinal by-pass means which extends from approximately the edge of the sleeve adjoining the collar to the rear end of the injection needle or the neck aperture. The room bounded by the inner walls of the sleeve, apart from the by-pass means, has the same rotationally symmetrical but a slightly longer shape than the sealing stopper, or, in the presence of a separating stopper, than the sealing stopper and the separating stopper together, and has approximately the same diameter as the inside diameter of the ampoule.

Such an injection syringe, more in particular intended for transport and storage while being filled with an injection liquid and for single dosage use, a so-called prefillable or pre-filled syringe, is disclosed in U.S. Pat. No. 4,235,235. The syringe disclosed in this Patent comprises a by-pass means for the injection liquid in the form of one or more slots recessed in the inner wall of the needle holder. When said syringe is used, the sealing stopper is pushed forwards, by exerting pressure on the plunger, into the sleeve of the needle holder. The rear part of the slot or slots becomes uncovered, so that the injection liquid can easily reach the injection needle through the slot or slots and can be expelled. In most of the embodiments shown, the needle is connected centrally to the needle holder sleeve. One embodiment shows an eccentrically provided needle; this embodiment may be desired in syringes having a large ampoule diameter.

It occurs more and more frequently that doctors or nurses administer an injection without previously deaerating the injection syringe, the so-called "piqûre-directe" method. In some cases it may even be very desirable not to deaerate the syringe, for example, in case of heparin-filled syringes which are used for operation patients; upon deaerating, the outside of the needle could easily be wetted with heparin prior to the injection, so that afterbleeding of the injection wound is promoted. In case the syringe known from the above Patent is used for administering an injection without deaerating, the air present in the needle holder sleeve in front of the sealing stopper is also injected. This is a great disadvantage because this air reaches the blood circulation system of the patient and hence may cause an air embolism in particular in intravenous injections. It is therefore desired to minimize the amount of air which is injected together with the injection liquid. A possibility to that end might be to reduce the length of the sealing stopper and hence of the needle holder sleeve. However, a thinner stopper involves the risk of leakage and evaporation of injection liquid so that the improvement is not set off against the associated disadvantages.

It is the object of the present invention to provide an injection syringe with which the so-called "piqûre-directe" method may be used without any objection but while maintaining the advantages of the syringe known from U.S. Pat. No. 4,235,235, such as reliability, sterility of its interior, no particulate matter in the liquid to be injected, a small dead space for injection liquid, a low resistance during injection, a comparatively thick stopper so that little diffusion will occur, and a comparatively small number of simple components so that the costs of manufacture can be kept low.

This object can be achieved by means of an injection syringe of the kind mentioned in the opening paragraph which is characterized according to the invention in that the by-pass means comprises at least one duct recessed in the side wall of the sleeve and communicating said room with said neck aperture of the needle holder, which said duct, from approximately the rear edge of the sleeve over a part of its length considerably smaller than the length of the sealing stopper, is in open communication with the room but for the remaining part is separated therefrom, in that an aperture is recessed in the front end of the sleeve in its end wall or in its side wall close to said end wall, said aperture communicating said room in the sleeve with the exterior, and in that means are provided to keep the aperture in the front end of the sleeve, as well as the injection needle or the neck aperture in a sterile condition.

In a preferred embodiment the injection syringe of the invention is characterized in that the needle holder neck is provided eccentrically on the outside of the end wall of the sleeve, in that one duct is recessed in the side wall of the needle holder sleeve, which duct and the neck aperture are in the elongation of each other, and in that the aperture in the front end of the sleeve is positioned at its end wall.

The eccentric position of the neck destined for the connection of the injection needle serves first of all for obtaining a good communication of the recessed duct to the neck aperture so that the injection liquid can easily reach the injection needle. Furthermore, on the front of the needle holder there must be sufficient space for an aperture through which the air in front of the sealing stopper can escape to the exterior when the syringe is used. The eccentric position of the neck on the needle holder sleeve hence serves quite a different purpose from that for the eccentric needle arrangement in the known construction mentioned hereinbefore. In the know syringe, a needle holder with eccentrically situated needle may be used in combination with an ampoule having a large diameter to facilitate the administration of an injection. In contrast herewith, syringe according to the present invention are destined in particular for injecting small doses of injection liquid because in this case the "piqûre-directe" method is most frequently used and, in case the known syringe is used, the amount of air also injected is relatively largest. This aspect will be further explained hereinafter.

An advantage of the neck placed eccentrically on the needle holder sleeve for the connection of the injection needle is that the duct recessed in the side wall of the sleeve and the neck aperture can be in the elongation of each other so that the front part of the duct together with the neck aperture may serve for the connection of the injection needle. The assembly of ampoule, injection needle or neck for the connection thereof, covered with protective means may thus be shorter, hence more compact, as a result of which the syringe can more easily be packaged and handled during use.

In case an injection syringe is preferred, having the needle holder neck, and hence the injection needle, centrally positioned on the outside of the end wall of the needle holder sleeve, a bipartite construction of the needle holder is preferred. A suitable embodiment of an injection syringe of the invention provided with a centrally positioned needle is characterized in that the needle holder consists of two portions, the one portion comprising the collar and the sleeve and the other portion comprising the neck, the said one portion including the said duct in the wall of the sleeve, communicating with at least one slot radially recessed in the front face of said end wall of the sleeve, and the neck portion being provided with a radially outwardly extending flange having a substantially equally large diameter as the end wall of the sleeve, said flange being sealingly connected at its circumferential edge with the front face of the end wall of the sleeve in such manner, that the neck aperture communicates with the slot recessed in the end wall of the sleeve.

The favourable properties of the injection syringe according to the invention will become most apparent from a description of the use of the syringe. When the syringe is used, first the protective means covering the injection needle is removed. The injection needle connected in the neck aperture of the needle holder may then be inserted into the patient's body, if desired without deaeration. In case the needle is supplied separately, it should first be connected to the neck after removing its protective means. By exerting pressure on the plunger by means of the plunger rod, the sealing stopper is pushed forward into the needle holder sleeve. The air present in the sleeve in front of the stopper escapes through the aperture in the front end of the sleeve. When the stopper has moved forward sufficiently far into the needle holder sleeve, the entrance to the duct in the side wall of the sleeve has become uncovered, so that the injection liquid can reach the injection needle through said duct and can thus be injected into the patient. At the same time the stopper has moved forward in the sleeve over such a distance that its circumference adjoins the inner wall of the sleeve in a sealing manner, so that the injection liquid cannot reach the room in front of the stopper and consequently cannot reach the aperture in the front end of the sleeve either.

The aperture in the front end of the needle holder sleeve must be sufficiently wide so that the air can be easily escape from the room in front of the stopper without it being possible for pressure to build up in said room.

The aperture recessed in the front end of the needle holder sleeve and the injection needle or the neck aperture for connecting the injection needle are preferably covered jointly by means of one protective cover which can be connected to the needle holder. For that purpose, connection means for the protective cover are provided on the outside of the needle holder. Examples of suitable connection means are a circumferential groove recessed in the outside of the needle holder, or a radialy outwardly projecting circumferential edge or ridge provided on its outside, suitable for engagement in respectively a radially projecting circumferential edge or ridge or a circumferential groove on or in the inner wall of the protective cover, which is manufactured from a slightly resilient material. By such a snap-cap construction a good sterile sealing is obtained, while the protective cover can easily be removed very simply before use of the syringe. Alternatively, the injection needle can be kept in a sterile condition by covering this needle with a well-known needle guard, and the aperture in the front end of the sleeve by sealingly inserting therein a bacterial filter.

It is structurally attractive to construct the rear face of the end wall of the needle holder sleeve and the front face of the sealing stopper in such manner that they are substantially complementary with respect to each other; these faces are preferably subtantially flat surfaces. The rear face of the stopper and the front face of the plunger preferably are also constructed so that after injecting the injection liquid they adjoin each other as well as possible to minimize the residual volume of injection liquid in the syringe. The invention also relates to a two-chamber syringe of a type as described in the published European Patent Application No. 72058. In such a syringe, two different injection liquids are accomodated in the ampoule and are separated from each other by a stopper, the length of the needle holder sleeve being slightly larger than the length of the sealing stopper and the separating stopper together. In a syringe according to the invention in a two-chamber construction, the rear face of the sealing stopper and the front face of the separating stopper, as well as the rear face of the separating stopper and the front face of the plunger are preferably complementary as well as possible, so that after use of the syringe the residual volume of injection liquid in the syringe is minimal.

The syringe according to the invention is intended more in particular to be transported, while being filled with injection liquid, and to be used only once. In the empty condition such a syringe is termed a prefillable syringe, when filled with one or two injection liquids, a prefilled syringe. In the latter case the ampoule is filled with an injection liquid or with two injection liquids separated from each other by a separating stopper, the front end of the ampoule being sealed by the sealing stopper which is situated entirely within the ampoule.

For practical and economical reasons it is of advantage to use a minimum number of different components for a syringe. As a result of this the risk of interchanging components during assembly is restricted, while the manufacture of components in larger quantities will reduce the price of the components. As a plunger is preferably used a rotationally symmetrical, more or less cylindrical body of a resilient material closed at one end and to the other end of which a plunger rod can be connected, for example, by screwing or clamping. For example, a simple clamping connection can be obtained by recessing in the above-mentioned other end of the plunger an aperture which, for example, is widened on the side of the closed end so as to be able to receive a thickened end portion of the plunger rod. In that case it is advantageous to use an identical body as a sealing stopper for the prefilled syringe, plunger and sealing stopper being positioned oppositely in the ampoule on each side of the injection liquid. The extra quantity of air which is present in the cavity of the sealing stopper is no objection, because the said air is not also injected but can escape through the aperture in the front end of the needle holder sleeve.

As already noted hereinbefore, the syringe according to the present invention is destined in particular for injecting small doses of injection liquid, for example, doses of less than approximately 1 ml, because the advantages of the syringe then are most prominent. In order to be able to expel such small doses as completely as possible, hence to keep the residual liquid as minimal as possible, it is of advantage that the inside diameter of the ampoule is at most approximately 6 mm.

As already indicated hereinbefore, the invention is not restricted to syringes already provided with an injection needle, but it also covers syringes which are supplied in the prefillable or prefilled condition without the injection needle being assembled. In the latter case, the user himself can select, prior to use, the best suitable needle from the needles supplied with the syringe and, of course after removing the protective cover, connect it to the needle holder neck. A connecting means suitable for this purpose is a Luer cone or a Luer lock cone. By means of a needle cone, connected around the needle near its rear tip, the needle is slid on the neck of the needle holder, needle cone and neck fitting exactly into each other so that the parts are connected in a clamping manner. In a Luer lock cone there is in addition a simple screw connection between needle cone and needle holder neck.

The plunger and the stopper or stoppers are manufactured from a resilient material. The barrel is preferably manufactured from glass but may also be manufactured from a suitable form-retaining synthetic material when said material does not have an adverse influence on the quality of the injection liquid. The needle holder is preferably manufactured from one assembly by injection moulding from a suitable form-retaining synthetic material. When an ampoule of synthetic material is used, ampoule and needle holder may be made integrally by injection moulding. It is advisable to carry out the injection moulding process under dust-free conditions so as to avoid dust particles in the needle holder. Normally, prior to assembling, the components of the syringe with which the injection liquid comes into contact, hence the ampoule, the stopper or stoppers, and the combination of needle holder, injection needle and needle cover, are sterilized.

The invention will now be described in greater detail with reference to embodiments which are shown in the drawings, in which:

FIG. 1 is a longitudinal sectional view of a syringe according to the invention in the condition in which it can be transported and stored;

FIG. 2 is a cross-sectional view through the needle holder of the syringe shown in FIG. 1, namely taken on the line II—II of FIG. 1, viewed in the direction of the injection needle;

FIG. 3 is a sectional view on an enlarged scale of a detail of a syringe comparable to that of FIG. 1, namely of the front end of the ampoule with the sealing stopper and of the needle holder with the injection needle, also in the condition prior to use of the syringe, but now after the protective cover has been removed;

FIGS. 4 and 5 show the same details on an enlarged scale as those of FIG. 3 but now during use of the syringe;

FIG. 6 is again the same detail on an enlarged scale as in FIGS. 3, 4 and 5 but now after all injection liquid has been expelled;

FIG. 7 is a longitudinal sectional view of a syringe according to the invention in a different embodiment, in the condition in which it can be transported and stored;

Figures 3, 4:
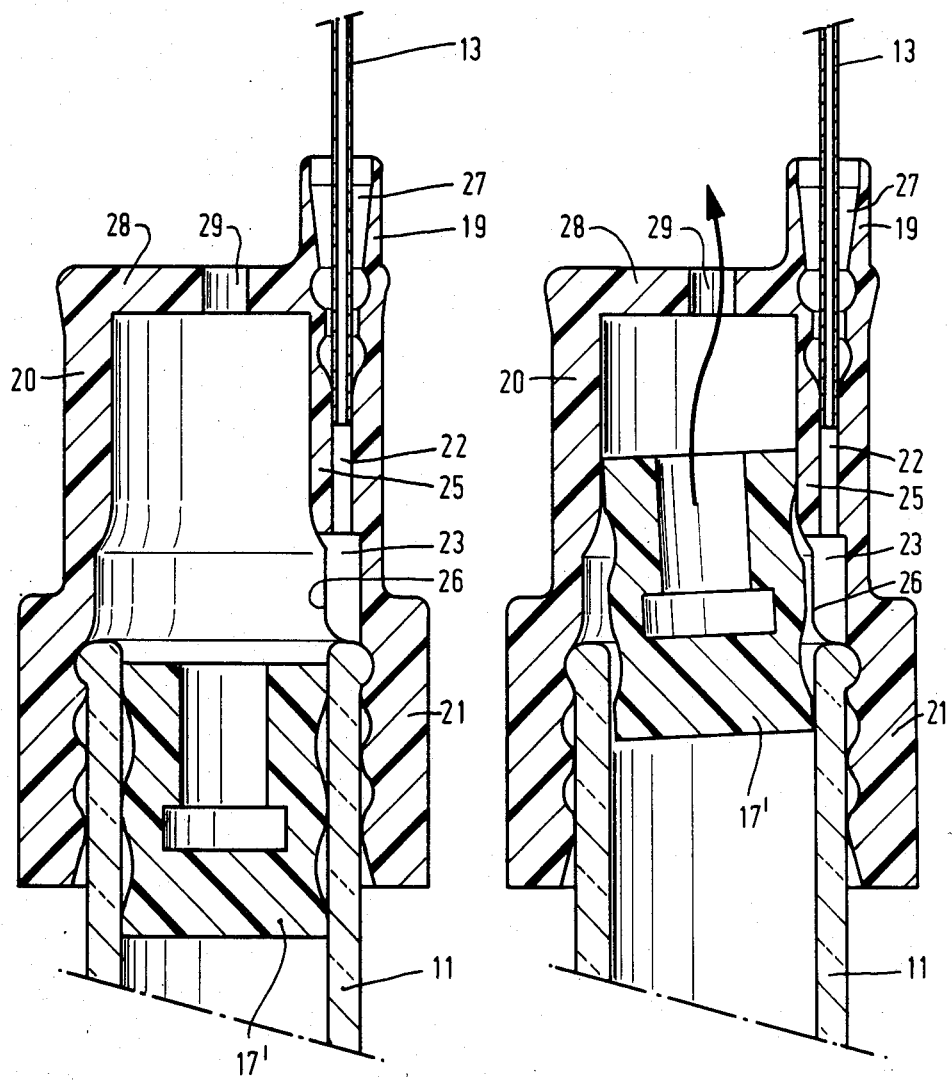

FIG. 8 shows a top view of the needle holder sleeve of the syringe shown in FIG. 7 at the position where the flange of the neck portion of the needle holder is connected to the needle holder sleeve, viewed in the direction of the ampoule; and FIG. 9 is a cross-sectional view through the needle holder sleeve of the syringe shown in FIG. 7, taken on the line IX—IX of FIG. 7, viewed in the direction of the injection needle.

The syringe shown in FIG. 1 comprises an ampoule 11 in which a plunger 12 is provided at one end while the other end comprises an injection needle 13 enclosed in a protective cover 14.

The plunger can be moved by means of a plunger rod 15 which is mounted on the plunger by means of a screwed connection 24. At the same end where the plunger is present, the ampoule comprises on its outside a finger grip 16 which is connected around the ampoule according to the so-called snap-cap principle. The finger grip preferably consists of slightly resilient but form-retaining material, for example, a synthetic material. The ampoule is manufactured from a rigid material, preferably glass. In another suitable embodiment, the finger grip is a flange-like part of the ampoule which extends radially outwards.

A sealing stopper 17 is present in the end of the ampoule remote from the plunger. When used as a two-chamber syringe a separating stopper is also present in the ampoule and keeps the two injection liquids separated from each other. The stopper or stoppers are manufactured from a resilient material, preferably from rubber of a pharmaceutical quality.

The injection needle 13 is connected to the ampoule by means of a needle holder 18. The needle holder consists of a neck 19 which keeps the needle sealingly connected in a clamping manner, a sleeve 20 and a collar 21. The needle holder is preferably manufactured by injection moulding from a slightly resilient material which, however, is sufficiently form-retaining, for example a synthetic material, and is connected to the end of the ampoule by means of a snap-cap construction.

In the side wall of the needle holder sleeve a duct 22 is recessed, the rear part 23 of which is in open communication with the room inside the sleeve but the remaining part of which is separated therefrom by means of wall portion 25. As is shown in FIG. 1, the needle holder sleeve is slightly asymmetrical in that the wall part in which the duct 22 is recessed is somewhat thicker than the oppositely located wall part. In order to facilitate the transition of the sealing stopper 17 from the barrel to the sleeve during use of the syringe, the rear portion 26 of the inner wall of the sleeve is slightly widened, the widened portion graduallly changing into the remaining part of the sleeve with constant inside diameter, approximately equally large as that of the ampoule. The duct 22 communicates with the interior of the injection needle 13 connected in the neck aperture 27. A circular aperture 29 is recessed in the end wall 28 of the sleeve 20. FIG. 2 is a cross-sectional view through the needle holder sleeve taken on the line II—II of FIG. 1, viewed in the direction of the needle.

The most essential part of a syringe comparable to the FIG. 1 syringe is shown on an enlarged scale in FIG. 3. As a difference with the syringe shown in FIG. 1, the syringe of FIG. 3 comprises a sealing stopper 17' comprising a cavity and being identical to the plunger 12' (see FIG. 6), but which is placed in the ampoule in a position opposite to the plunger.

FIGS. 4 and 5 show the same detail enlargement of FIG. 3 but this time when the syringe is in use. As is shown in FIG. 4, first the sealing stopper 17' is moved forward, the air present in the sleeve escaping through the opening 29; this is indicated by means of an arrow. Via the gradual transition 26 in the needle holder the sealing stopper is received with friction by the portion of the needle holder sleeve of equal diameter. Therefore, the inside diameter of that portion of the sleeve is approximately equal to that of the ampoule. As is shown in FIG. 5, when the sealing stopper 17' is further moved forward, the rear part of duct 22 (the part 23 adjoining the ampoule), which is in open communication with the room inside the needle holder sleeve 20 has become uncovered so that the injection liquid 30 behind the sealing stopper 17' can without any hindrance reach the interior of the injection needle 13 via the duct 22 and can be expelled; this is also indicated by means of an arrow in FIG. 5. Because the sealing stopper is inserted in the needle holder sleeve so as to be circumferentially sealing, no injection liquid can reach the room in front of the sealing stopper and leak away to the exterior via the opening 29. In order to ensure an unhindered passage of the injection liquid, the cross-section of duct 22 is at least equally large as that of the interior of the injection needle 13. As will be obvious from the Figures, the needle holder sleeve is slightly longer than the sealing stopper, so that the sealing stopper can move forward unhindered over such a distance that the entrance 23 to the duct 22 has become uncovered for the injection liquid. When used as a two-chamber syringe, the needle holder sleeve should be slightly longer than the sealing stopper and separating stopper together. FIG. 6 finally shows the condition after the injection liquid has been expelled. The front face of the sealing stopper 17' then bears against the rear face of the end wall 28 of the needle holder sleeve 20, while the front face of the piston 12' and the rear face of the sealing stopper 17' are pressed against each other to minimize the amount of residual injection liquid in the syringe.

In the syringe shown in FIGS. 3-6 a plunger rod having a thickened end may be inserted in recess 31 of the plunger.

In another embodiment which is not shown in the drawings the neck 19 of the needle holder may externally be constructed with a Luer cone or Luer lock cone.

The syringe shown in FIGS. 7-9 is constructed for the greater part as the syringe of FIG. 1, with the exception of the needle holder. Components corresponding with those of the syringe shown in FIG. 1 are denoted with the same reference numerals, viz. ampoule 11, plunger 12, injection needle 13, protective cover 14, plunger rod 15, finger grip 16 and sealing stopper 17. The injection needle is connected to the ampoule by means of a needle holder 32, the collar 33 of which is sealingly clamped on the ampoule. The needle holder further comprises a neck 34 sealingly connecting the injection needle, and a sleeve 35 between collar and neck. The needle holder is manufactured from a synthetic material, preferably as indicated for the syringe shown in FIG. 1, and comprises two portions, viz. a neck portion comprising the neck and a flange 36, and a portion comprising the collar and the sleeve. The sleeve is closed at its front end with an end wall 37, the front face of which with its circumferential edge being sealingly connected to the flange 36 of the neck portion, for example, by welding or luting. In the side-wall of the sleeve a duct 38 is recessed communicating with a slot 39 radially recessed in the front face of the end wall 37, which slot communicates with the neck aperture. A portion of the duct 38, viz. at 40, is in open communication with the room in the needle holder sleeve. The length of this open communication 40 is considerably smaller than the length of the sealing stopper 17. In the front end of the sleeve in its side wall an aperture 41 is recessed. Both the injection needle 13 and the aperture 41 in the needle holder sleeve are covered with protective cover 34 to keep the interior of the syringe in a sterile condition.

In a slightly different embodiment the aperture 41 is positioned at the front of the needle holder next to the needle holder neck and is formed by apertures recessed in end wall 37 and in flange 36, both apertures communicating with each other.

In a further different embodiment the protective cover is replaced by a needle guard, sealingly connected on the neck 34 of the needle holder and covering the needle. In that case a bacterial filter is sealingly positioned within aperture 41.

I claim:

1. An injection syringe comprising a hollow cylindrical ampoule which is open at both ends, a plunger which is movable in the ampoule and seals same, a sealing stopper the dimensions of which are such that it can be provided in a sealing manner in the front end of the ampoule, optionally a separating stopper to be provided in the ampoule so as to be movable and in a sealing manner in order to be able to keep two different injection liquids, if present in the ampoule, separated from each other prior to use of the syringe, and a needle holder comprising a collar connected to the front end of the ampoule in a sealing manner, and an inwardly subtantially cylindrical sleeve closed at its front end by means of a wall, said end wall comprising on the outside a neck in the aperture of which or to which an injection needle is or can be connected in a sealing manner, the side wall of the sleeve comprising over approximately the full length a longitudinal by-pass means which extends from approximately the edge of the sleeve adjoining the collar to the rear end of the injection needle or the neck aperture, and in which the room bounded by the inner walls of the sleeve, apart from the said by-pass means, has the same rotationally symmetrical but a slightly longer shape than the sealing stopper, or, in the presence of a separating stopper, than the sealing stopper and the separating stopper together, and has approximately the same diameter as the inside diameter of the ampoule, characterized in that the by-pass means comprises at least one duct recessed in the side wall of the sleeve and communicating said room with said neck aperture of the needle holder, which said duct, from approximately the rear edge of the sleeve over a part of its length considerably smaller than the length of the sealing stopper, is in open communication with the said room but for the remaining part is separated therefrom, in that an aperture is recessed in the front end of the sleeve in its end wall or in its side wall close to said end wall, said aperture communicating said room in the sleeve with the exterior, and in that means are provided to keep the said aperture in the front end of the sleeve, as well as the injection needle or the neck aperture in a sterile condition.

2. A syringe as claimed in claim 1, characterized
in that the needle holder neck is provided eccentrically on the outside of the end wall of the sleeve,
in that one duct is recessed in the side wall of the needle holder sleeve, which duct and the neck aperture are in the elongation of each other, and
in that the aperture in the front end of the sleeve is positioned at its end wall.

3. A syringe as claimed in claim 1, characterized in that the needle holder consists of two portions, the one portion comprising the collar and the sleeve and the other portion comprising the neck, the said one portion including the said duct in the side wall of the sleeve, communicating with at least one slot radially recessed in the front face of said end wall of the sleeve, and the said neck portion being provided with a radially outwardly extending flange having a substantially equally large diameter as the end wall of the sleeve, said flange being sealingly connected at its circumferential edge with the front face of the said end wall of the sleeve in such manner, that the neck aperture communicates with the said slot recessed in the said end wall of the sleeve.

4. A syringe as claimed in any of the preceding claims, characterized in that the outside of the needle holder comprises means for connecting a protective cover, and that the aperture recessed in the front end of the needle holder sleeve together with the injection needle or the neck aperture are sealingly covered by one protective cover.

5. A syringe as claimed in any of the preceding claims, characterized in that the rear face of the said end wall of the needle holder sleeve and the front face of the sealing stopper are substantially complementary and preferably substantially flat surfaces.

6. A syringe as claimed in any of the preceding claims, in which the ampoule is filled with an injection liquid or with two different injection liquids separated from each other by a separating stopper, and in which the front end of the ampoule is sealed by the sealing stopper which is situated entirely within the ampoule.

7. A syringe as claimed in claim 6, characterized in that plunger and sealing stoppper are identical, rotationally symmetrical bodies closed at one end and manufactured from a resilient material, in the open other end of which a plunger rod can be connected, and that plunger and sealing stopper are oppositely positioned in the ampoule.

8. A syringe as claimed in any of the preceding claims for injecting doses of injection liquids of less than approximately 1 ml, characterized in that the inside diameter of the ampoule is at most approximately 6 mm.

9. A needle holder for a syringe as claimed in claim 2, comprising a collar and an inwardly substantially cylindrical sleeve which is closed at its front end by means of a wall, which end wall on its outside comprises a neck in the aperture of which or to which an injection needle can be connected in a sealing manner, the side wall of the sleeve comprising over approximately the full length a longitudinal by-pass means which extends from approximately the edge of the sleeve adjoining the collar to the neck aperture, the sleeve having a substantially equally large diameter as the ampoule to be connected to the needle holder, characterized
in that the by-pass means comprises at least one duct which is recessed in the side wall of the sleeve and is in open communication with the room bounded by the inner walls of the sleeve from approximately the rear edge of the sleeve over a part of its length, but for the remaining part is separated from the said room,
in that the needle holder neck is provided eccentrically on the outside of the end wall of the sleeve,
in that the duct recessed in the side wall of the sleeve and the neck aperture are in the elongation of each other, and
in that an aperture is recessed in said end wall.

10. A needle holder for a syringe as claimed in claim 3, comprising a collar and an inwardly substantially cylindrical sleeve which is closed at its front end by means of a wall, which end wall on its outside comprises a neck in the aperture of which or to which an injection needle can be connected in a sealing manner, the side wall of the sleeve comprising over approximately the full length a longitudinal by-pass means which extends from approximately the edge of the sleeve adjoining the collar to the neck aperture, the sleeve having a substantially equally large diameter as the ampoule to be connected to the needle holder, characterized
in that the by-pass means comprises at least one duct which is recessed in the side wall of the sleeve and is in open communication with the room bounded by the inner walls of the sleeve from approximately the rear edge of the sleeve over a part of its length, but for the remaining part is separated from the said room,
in that an aperture is recessed in the front end of the sleeve in its end wall or in its side wall close to said end wall, and
in that the needle holder consists of two portions, the one portion comprising the collar and the sleeve and the other portion comprising the neck, the said one portion including the said duct in the side wall of the sleeve, communicating with at least one slot radially recessed in the front face of said end wall of the sleeve, and the said neck portion being provided with a radially outwardly extending flange having a substantially equally large diameter as the end wall of the sleeve, said flange being sealingly connected at its circumferential edge with the front face of the said end wall of the sleeve in such manner, that the neck aperture communicates with the said slot recessed in the said end wall of the sleeve.

11. A needle holder as claimed in claim 9 or 10, characterized in that the needle holder comprises on its outside means for connecting a protective cover capable of sealingly covering the aperture recessed in the end wall of the needle holder sleeve together with the injection needle to be connected to the needle holder neck or in the neck aperture.

* * * * *